（12） United States Patent
Tinsley et al.

(10) Patent No.: US 9,877,928 B2
(45) Date of Patent: Jan. 30, 2018

(54) GEAR DRIVE DAMPER

(75) Inventors: Barton Tinsley, Beverly Hills, MI (US); Charles Shepard, Davisburg, MI (US)

(73) Assignee: Air Systems, Inc., Royal Oak, MI (US)

( * ) Notice: Subject to any disclaimer, the term of this patent is extended or adjusted under 35 U.S.C. 154(b) by 1252 days.

(21) Appl. No.: 12/227,885

(22) PCT Filed: May 30, 2007

(86) PCT No.: PCT/US2007/012722
§ 371 (c)(1),
(2), (4) Date: Dec. 1, 2008

(87) PCT Pub. No.: WO2007/142957
PCT Pub. Date: Dec. 13, 2007

(65) Prior Publication Data
US 2009/0264063 A1 Oct. 22, 2009

Related U.S. Application Data

(60) Provisional application No. 60/809,258, filed on May 30, 2006.

(51) Int. Cl.
*F24F 13/14* (2006.01)
*A61K 31/05* (2006.01)
*A61K 31/352* (2006.01)

(52) U.S. Cl.
CPC ............ *A61K 31/05* (2013.01); *A61K 31/352* (2013.01)

(58) Field of Classification Search
CPC ............................... F24F 13/12; F24F 13/1426
USPC ................ 454/324, 333, 330, 228, 331, 332
See application file for complete search history.

(56) References Cited

U.S. PATENT DOCUMENTS

| 1,504,507 | A | * | 8/1924 | Richardson | 251/212 |
| 2,203,587 | A | * | 6/1940 | Young | E05F 11/40 49/138 |
| 3,034,531 | A | * | 5/1962 | Kennedy | 137/601.04 |
| 3,572,158 | A | * | 3/1971 | Adams | 74/498 |
| 3,746,042 | A |   | 7/1973 | Finkel | |
| 3,847,210 | A | * | 11/1974 | Wells | 165/103 |

(Continued)

FOREIGN PATENT DOCUMENTS

JP 04142366 A * 5/1992

OTHER PUBLICATIONS

International Search Report for PCT/US2007/12722 dated Mar. 14, 2008.

*Primary Examiner* — Alissa Tompkins
*Assistant Examiner* — Phillip E Decker

(57) ABSTRACT

An air damper assembly for regulating an air flow includes a frame, a plurality of elongated damper blade rotatably mounted to the frame, and a drive mechanism for actuating the damper blades between open and closed positions. The drive mechanism includes a gear fixedly secured to a distal end of each of the damper blades and an elongated rack slidably coupled to the frame. The rack meshingly engages the gears such that linear movement of the rack in a first linear direction results in rotational movement of the damper blades in a first rotational direction and linear movement of the rack in a second linear direction opposite the first linear direction results in rotational movement of the damper blades in a second, rotational direction opposite the first rotational direction.

16 Claims, 7 Drawing Sheets

(56) References Cited

U.S. PATENT DOCUMENTS

| | | | |
|---|---|---|---|
| 4,006,692 A | | 2/1977 | Chierici |
| 4,593,578 A | * | 6/1986 | Kobayashi et al. ............ 74/498 |
| 4,680,981 A | * | 7/1987 | Downing ............... B62D 3/123 |
| | | | 29/434 |
| 5,537,780 A | * | 7/1996 | Cleaver et al. ................ 49/82.1 |
| 5,839,548 A | * | 11/1998 | Parker et al. ................ 188/82.1 |
| 5,938,524 A | * | 8/1999 | Cunningham, Jr. .......... 454/234 |
| 5,959,956 A | * | 9/1999 | Takishima ......... G11B 17/0402 |
| | | | 360/99.07 |
| 6,099,405 A | | 8/2000 | Cunningham |
| 7,389,609 B2 | * | 6/2008 | Yorgason ....................... 49/82.1 |
| 2005/0076569 A1 | * | 4/2005 | Griffiths et al. ............... 49/82.1 |
| 2005/0252086 A1 | * | 11/2005 | Yorgason ....................... 49/82.1 |

* cited by examiner

GEAR DRIVE DAMPER

CROSS REFERENCE TO RELATED APPLICATIONS

This is a National Stage application and claims priority to and all the benefits of International Application No. PCT/US2007/012722, filed on May 30, 2007, which claims priority to and all the benefits of U.S. Provisional Application No. 60/809,258, filed on May 30, 2006 and entitled "Gear Drive Damper."

BACKGROUND OF THE INVENTION

1. Field of the Invention

The invention relates to air damper assemblies particularly for heating, ventilating and air conditioning systems. More particularly, the invention relates to air damper assemblies of the type that have a plurality of damper blades mounted for pivotal movement to regulate the volume of air that can be passed therethrough, or to completely block such air flow.

2. Description of the Related Art

Air damper assemblies including moveable louvers or damper blades for regulating air flow or completely blocking such air flow are well known in the art. Generally, an air damper assembly includes a rectangular frame for mounting of the air damper assembly in a suitable position with respect to the air flow. The frame includes a frame opening defining a flow area through which the air flow passes.

A plurality of damper blades, all of which are typically identical, is disposed horizontally within the frame opening. Each of the plurality of damper blades is generally rectangular in configuration and is rotatably mounted about its longitudinal central axis to the frame. Modulation of the plurality of damper blades determines the flow rate of the air flow by variably restricting the flow area of the frame opening. The flow area is maximized when the damper blades are rotated to an open position, whereat the damper blades are substantially coplanar with the air flow. Contrarily, the flow area is minimized, or even sealed tight, when the damper blades are rotated to a closed position, whereat the damper blades are transverse to the air flow.

Typically, the plurality of damper blades is coupled together and simultaneously actuated by a mechanical linkage. More specifically, a bracket or link is fixedly secured to each of the plurality of damper blades and a rod is pivotally connected to each link. The rod in turn is operatively coupled to an actuator, such as a pneumatic, electric, two-position, modulating, or spring return type actuator. Thus, linear movement of the rod by the actuator actuates the plurality of damper blades between the open and closed positions. Such mechanical linkages are complicated, include multiple connections and joints which leads to looseness or play in the linkage, are prone to failure, and are difficult to service. Consequently, it is desirable to provide an air damper assembly having an improved system for actuating or modulating a plurality of damper blades between open and closed positions.

SUMMARY OF THE INVENTION

According to one aspect of the invention, an air damper assembly is provided for regulating an air flow. The air damper assembly includes a frame that is adapted to be mounted in relationship to the air flow. The air damper assembly also includes a plurality of elongated damper blades rotatably mounted to the frame for rotational movement between an open position and a closed position. The air damper assembly further includes a drive mechanism for actuating the damper blades between the open and closed positions. The drive mechanism includes a gear that is fixedly secured to a distal end of each of the plurality of damper blades and an elongated rack that is slidably coupled to the frame. The rack meshingly engages the gears such that linear movement of the rack in a first linear direction results in rotational movement of the plurality of damper blades in a first rotational direction and linear movement of the rack in a second linear direction opposite the first linear direction results in rotational movement of the plurality of damper blades in a second rotational direction opposite the first rotational direction.

According to another aspect of the invention, an air damper assembly is provided for regulating an air flow. The air damper assembly includes a frame that is adapted to be mounted in relationship to the air flow. The air damper assembly also includes first and second elongated damper blades. Each of the first and second damper blades is rotatably mounted to the frame for rotational movement between an open position and a closed position. The air damper assembly further includes a drive mechanism for actuating the damper blades between the open and closed positions. The drive mechanism includes a gear that is fixedly secured to a distal end of each of the first and second damper blades, a first elongated rack that is slidably coupled to the frame, and a second elongated rack that is slidably coupled to the frame and is fixedly secured to the first rack. The first rack meshingly engages the gear on the first damper blade and the second rack meshingly engages the gear on the second damper blade. Linear movement of the first and second racks in a first linear direction results in rotational movement of the first damper blade in a first rotational direction and the second damper blade in a second rotational direction opposite the first rotational direction. Linear movement of the first and second racks in a second linear direction opposite the first linear direction results in rotational movement of the first damper blade in the second rotational direction and the second damper blade in the first rotational direction.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION OF THE PREFERRED EMBODIMENTS

Figure 1:
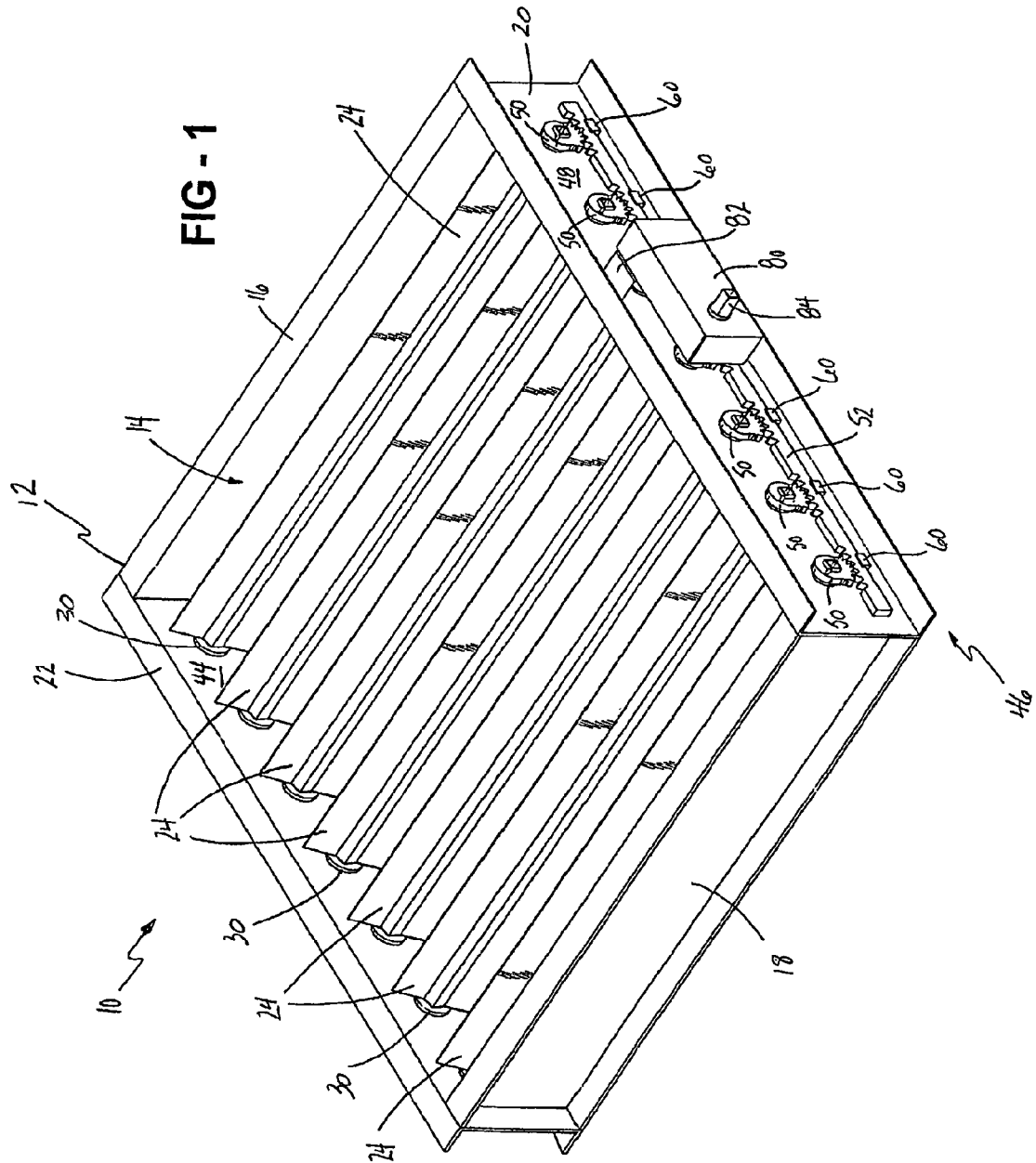
FIG. 1 is a perspective view of an air damper assembly including a drive mechanism according to one embodiment of the invention.
Figure 2:
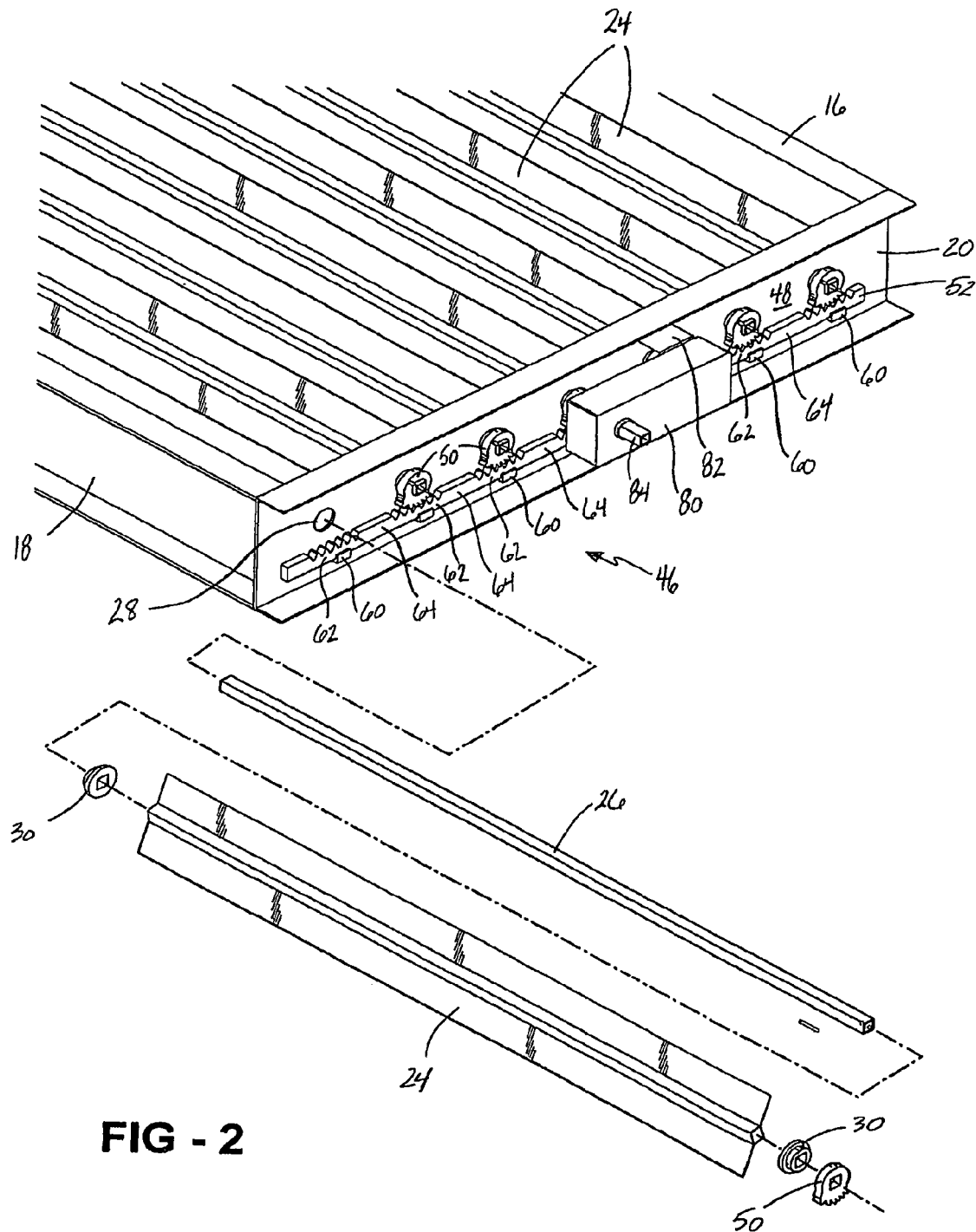
FIG. 2 is a partially exploded perspective view of the air damper assembly of FIG. 1.

Referring to FIGS. 1 and 2, an air damper assembly is generally shown at 10. The air damper assembly 10 includes a generally rectangular frame 12 adapted for mounting the air damper assembly 10 in fixed relationship within a supporting structure such as a wall opening of a building, a duct member, or the like. The frame 12 defines an air inlet opening 14 for receiving an air flow therethrough. The frame 12 includes a top member 16, a bottom member 18, and opposite side members 20, 22 which are formed of sheet metal or as an aluminum extrusion. In the embodiment shown, each of the top 16, bottom 18, and side 20, 22 members have a generally C-shaped cross-section to provide structural rigidity to the frame 12.

To permit the air flow through the air damper assembly 10 to be regulated or shut off, a plurality of parallel louvers or damper blades 24 are rotatably mounted within the air inlet opening 14. The damper blades 24 can also be formed of sheet metal, however, in the embodiment shown, the damper blades 24 are formed as an aluminum extrusion. The damper blades 24 extend horizontally across the air inlet opening 14. Each of the damper blades 24 is generally an elongated rectangular shaped member having a rod or shaft 26 extending through its longitudinal central axis and journalled within suitable openings 28 in the side members 20, 22 of the frame 12. More specifically, each opening 28 is a cylindrical bore extending through the respective side member 20, 22 of the frame 12. Each bore 28 is a close tolerance extrusion otherwise known to one skilled in the art as a pierced extrusion.

Figure 3:
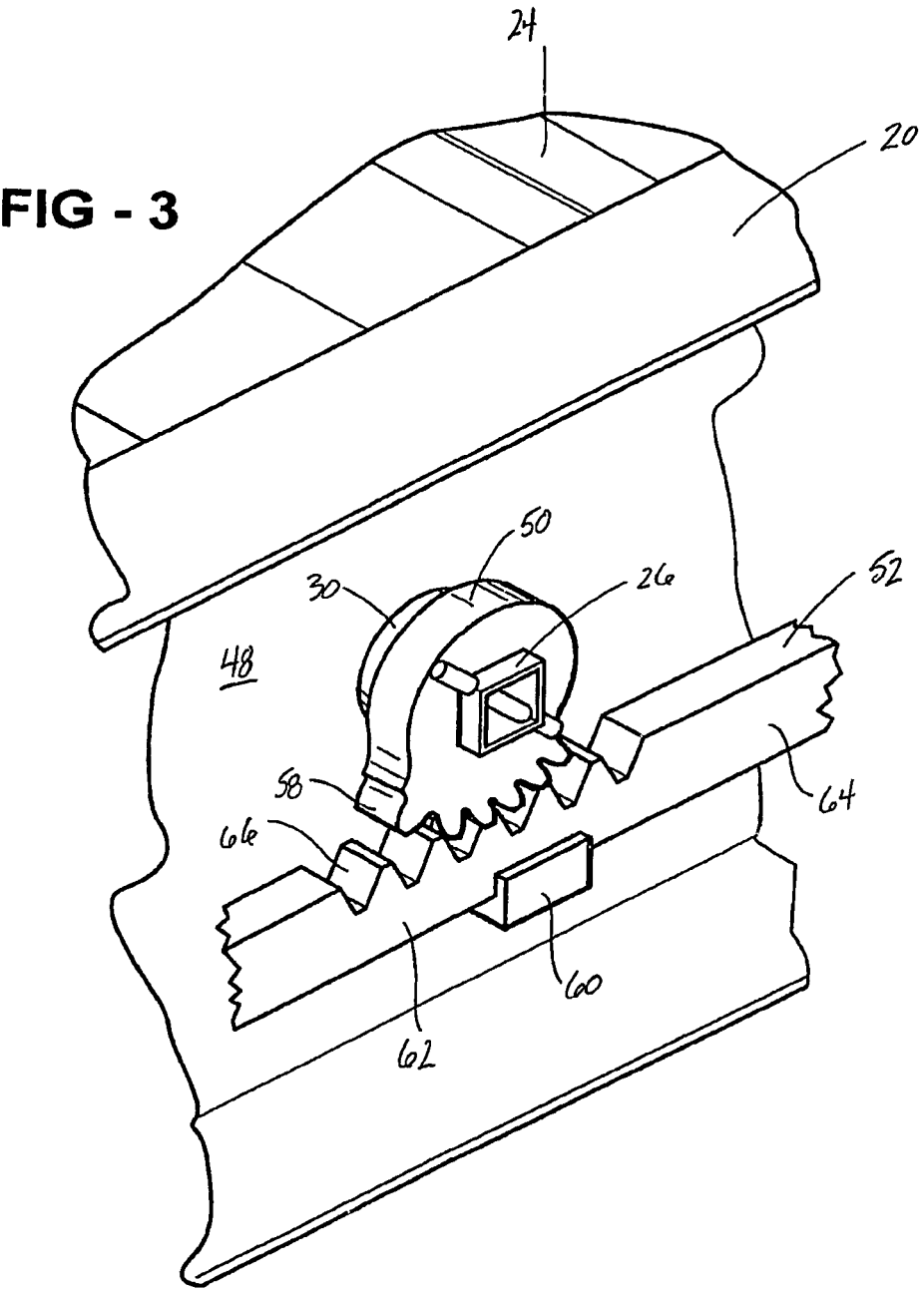
FIG. 3 is an enlarged, partially cut-away, perspective view of the air damper assembly of FIG. 1.
Figure 4:
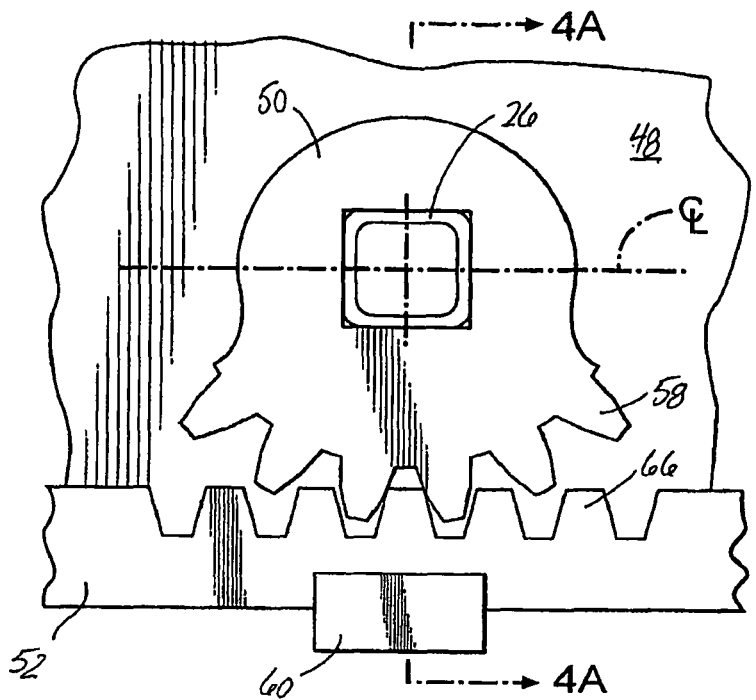
FIG. 4 is an enlarged, partially cut-away, side view of the air damper assembly of FIG. 1.
Figure 4A:
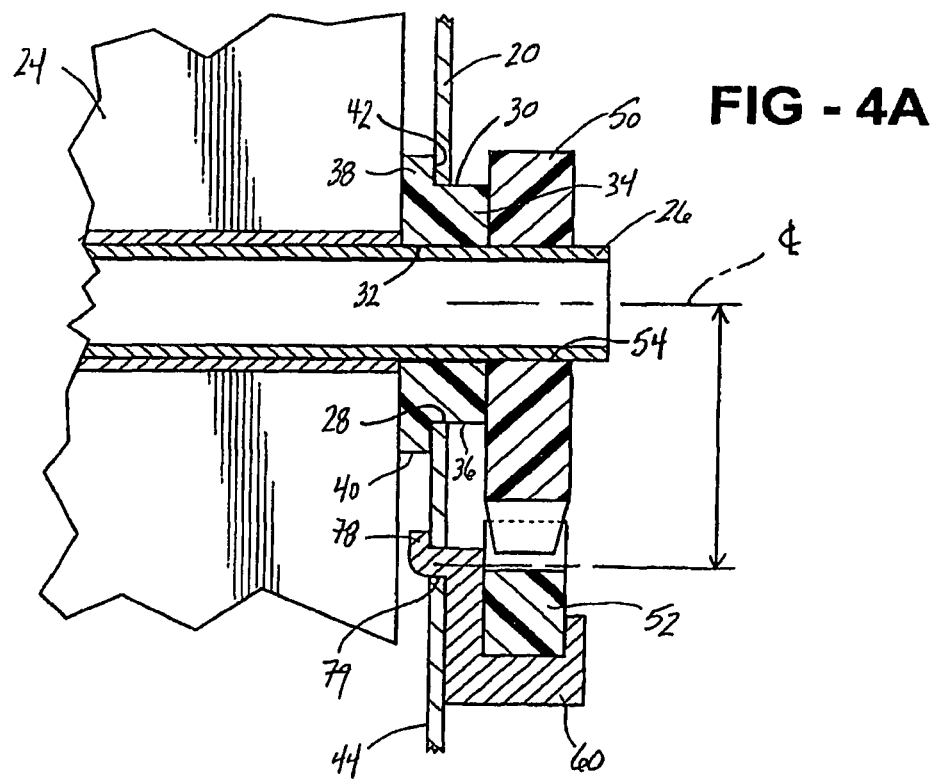
FIG. 4A is a cross-sectional view taken along lines 4-4 in FIG. 4.
Figure 5:
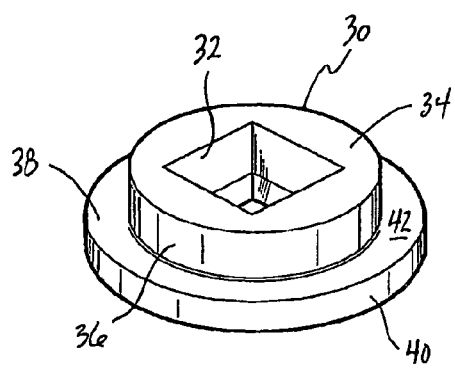
FIG. 5 is an enlarged perspective view of a bushing of the air damper assembly of FIG. 1.

Referring to FIGS. 3, 4A, and 5, a bushing 30, machined from ultra high molecular weight polyethylene (UHMW-PE), is rotatably disposed in each bore 28 and includes a square central aperture 32 through which a distal portion of the shaft 26 is disposed. Each bushing 30 also includes a first portion 34 having a first diameter 36 which is rotatably disposed within the bores 28 and a second portion 38 having a second diameter 40, which is larger than the first diameter 36. The second portion 38 defines a shoulder surface 42 for abutting against an interior surface 44 of the respective side members 20, 22 of the frame 12. The finish and tolerance of the first diameter 36 of the bushing 30 and the bore 28 in the respective side member 20, 22 of the frame 12 are such that the bushing 30 is a machine fit within the bore 28. Further, in the embodiment shown, each shaft 26 has a generally square cross-section such that as the shafts 26 rotate to move the damper blades 24, the bushings 30 rotate within the bores 28. The UHMW-PE material for the bushings 30 was chosen for its low coefficient of friction, to allow for low efforts while rotating the shafts 26. Additionally, because the bushings 30 are a non-ferrous material rotating in a ferrous part, the frame 12, the bushings 30 eliminate corrosion and seizure issues during the life of the air damper assembly 10.

The damper blades 24 rotate in common directions between an open position and a closed position. The flow area of the air inlet opening 14 is maximized when the damper blades 24 are rotated to the open position, whereat the damper blades 24 are substantially coplanar with the air flow. Contrarily, the flow area of the air inlet opening 14 is minimized, or even sealed tight, when the damper blades 24 are rotated to the closed position, whereat the damper blades 24 are transverse to the air flow.

Figure 6:
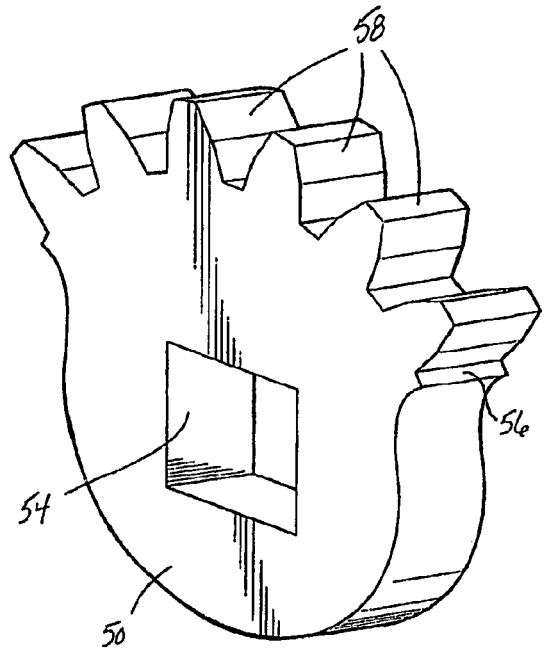
FIG. 6 is an enlarged perspective view of a gear of the air damper assembly of FIG. 1.

Referring to FIGS. 1 and 2, the damper blades 24 are operatively coupled together and are rotated simultaneously between the open and closed positions by a drive mechanism, generally shown at 46. The drive mechanism 46 is located along an exterior surface 48 of the side member 20 of the frame 12. The drive mechanism 46 includes a plurality of gears 50 supported by the shafts 26 and an elongated rack 52 extending between the gears 50. Each gear 50 is fixedly secured to one of the shafts 26 so that rotation of the gear 50 imparts rotation to the shaft 26, and in turn to the respective damper blade 24. In the embodiment shown, each gear 50 is formed of nylon and includes a square aperture 54 through which the distal portion of the shaft 26 is disposed, as shown in FIG. 6. Each gear 50 also includes a peripheral arcuate portion 56 having a plurality of gear teeth 58 extending therefrom. The nylon material for the gears 50 was chosen for its machinability and toughness in order to withstand the repetitive forces on the gear teeth 58.

Referring to FIGS. 1 through 4, the rack 52 is machined from a thermoplastic polymer, such as polyvinyl chloride (PVC), and is supported along the exterior surface 48 of the side member 20 by a plurality of rack supports 60 fixedly secured to the side member 20 as is described below in more detail. The rack 52 includes a plurality of toothed sections 62 spaced apart by non-toothed sections 64. Each toothed section 62 includes a plurality of rack teeth 66 extending therefrom. The PVC material for the rack 52 was chosen for its machinability and compressive strength. The gears 50 are oriented on the shafts 26 such that the gear teeth 58 meshingly engage with the rack teeth 66. It is therefore appreciated that linear movement of the rack 52 toward the top member 16 of the frame 12 will result in rotation of the gears 50 in a counterclockwise direction. Similarly, linear movement of the rack 52 toward the bottom member 18 of the frame 12 will result in rotation of the gears 50 in a clockwise direction.

Figure 7:
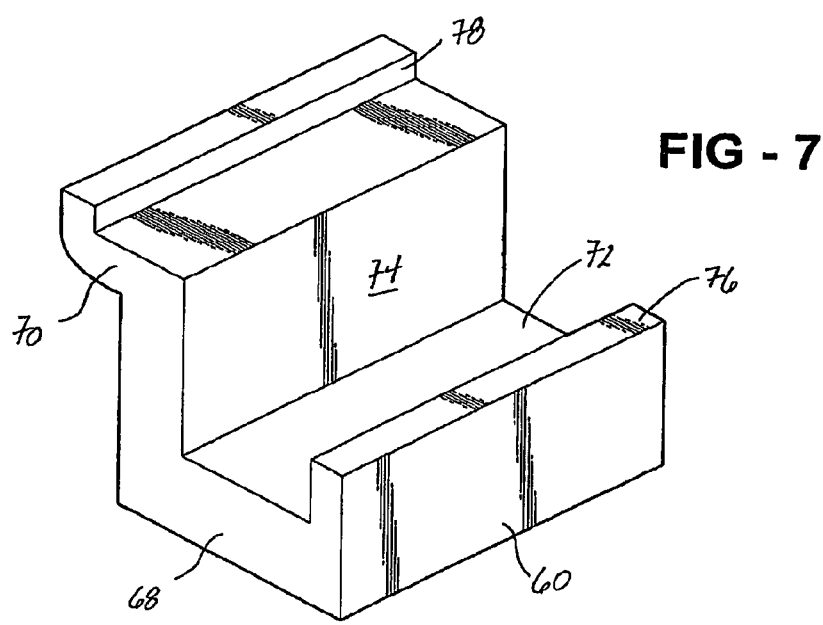
FIG. 7 is an enlarged perspective view of a rack support of the air damper assembly of FIG. 1.

In the embodiment shown, the number of rack supports 60 corresponds to the number of gears 50 such that there is one rack support 60 located directly below each one of the gears 50. It is appreciated, however, that more or less rack supports 60 can be used for supporting the rack 52 without varying from the scope of the invention. Each rack support 60 is machined from UHMW-PE and includes a lower portion 68 and an upper portion 70, as shown in FIG. 7. The lower portion 68 defines a channel 72 between a wall 74 and a raised lip 76 for slidably supporting the rack 52 therein. At a distal end of the wall 74, the upper portion 70 defines a clip 78 which snaps or clips into a rack support slot 79, best seen in FIG. 4A, in the side member 20 of the frame 12, thereby fixedly securing the rack support 60 to the frame 12. The UHMW-PE material for the rack supports 60 was chosen for its low coefficient of friction, to allow for easy sliding of the rack 52 along the rack supports 60, and flexibility for an interference fit between the rack 52 and the gears 50 as is described below in more detail.

The fit of the rack 52 and gears 50 versus a gear to gear fit is designed to eliminate almost all of the backlash. Backlash is purposeful clearance between mating components, sometimes described as the amount of lost motion due to clearance or slackness when movement is reversed and contact is re-established. In a pair of gears, backlash is the amount of clearance between mated gear teeth and allows for lubrication, manufacturing errors, deflection under load, and differential expansion between the gears. Backlash may be undesirable, however, in a positioning application where there are multiple gear to gear interfaces because of the small errors introduced at each interface. Such compounded errors may result in inaccurate operation of the positioning application. For example, in a large air damper assembly 10 having a high number of damper blades 24, the small amount of clearance introduced at each gear to gear interface would result in the damper blade 24 adjacent the top member 16 of the frame 12 being in the closed position while the damper blade 24 adjacent the bottom member 18 of the frame 12 is in the open position or a partially opened position. Any remaining backlash between the rack 52 and gears 50 is eliminated by holding tight tolerances on the machining of the gears 50, the rack 52, and the rack supports 60. Finally, the spacing that is held between the rack support slot 79 and a center line CL of the bores 28, as shown in FIG. 4A, establishes the interference fit between the rack 52 and gears 50. The flexibility of the rack supports 60 will absorb any deflection caused by the interference fit.

The drive mechanism 46 can be operated by an automatic actuator 80, a manual hand quadrant (not shown), or any of a variety of other types of actuators that are well known to one skilled in the art. Any style of automatic actuator 80 can be used, such as pneumatic, electric, two position, modulating, or spring return without varying from the scope of the invention. In the embodiment shown, the automatic actuator 80 is a two-position electric drive motor that is mounted to the side member 20 of the frame 12 with a bracket 82. The electric drive 80 is operatively coupled to an extended portion 84 of one of the shafts 26 which protrudes laterally from the side member 20 of the frame 12. While the shaft 26 with the extended portion 84 is located generally midway between the top 16 and bottom 18 members of the frame 12, it is appreciated that the shaft 26 with the extended portion 84 can be any one of the shafts 26 in the air damper assembly 10. It is contemplated that multiple air damper assemblies 10 can be operatively coupled together and actuated by a single actuator 80 by coupling or securing the rack 52 of a first air damper assembly 10 to the rack 52 of a second air damper assembly 10.

In operation, the electric drive 80 is actuated to rotate the damper blades 24 between the open and closed positions. Beginning with the damper blades 24 in the closed position, the electric drive 80 is actuated in a first direction such that the shaft 26 with the extended portion 84 rotates in the counterclockwise direction. Counterclockwise rotation of the shaft 26 with the extended portion 84 causes the gear 50 mounted thereon to also rotate in the counterclockwise direction. Meshing engagement between the gear teeth 58 of the gear 50 mounted on the shaft 26 with the extended portion 84 and the rack teeth 66 forces the rack 52 to move linearly toward the top member 16 of the frame 12. This linear movement of the rack 52 and meshing engagement between the rack teeth 66 and the gear teeth 58 of each gear 50 then causes the plurality of gears 50 to rotate in the counterclockwise direction such that the plurality of damper blades 24 rotates in the counterclockwise direction to the open position.

To return the damper blades 24 to the closed position, the electric drive 80 is actuated in a second direction such that the shaft 26 with the extended portion 84 rotates in the clockwise direction. Clockwise rotation of the shaft 26 with the extended portion 84 causes the gear 50 mounted thereon to also rotate in the clockwise direction. Meshing engagement between the gear teeth 58 of the gear 50 mounted on the shaft 26 with the extended portion 84 and the rack teeth 66 forces the rack 52 to move linearly toward the bottom member 18 of the frame 12. This linear movement of the rack 52 and meshing engagement between the rack teeth 66 and the gear teeth 58 of each gear 50 then causes the plurality of gears 50 to rotate in the clockwise direction such that the plurality of damper blades 24 rotates in the clockwise direction to the closed position.

Figure 8:
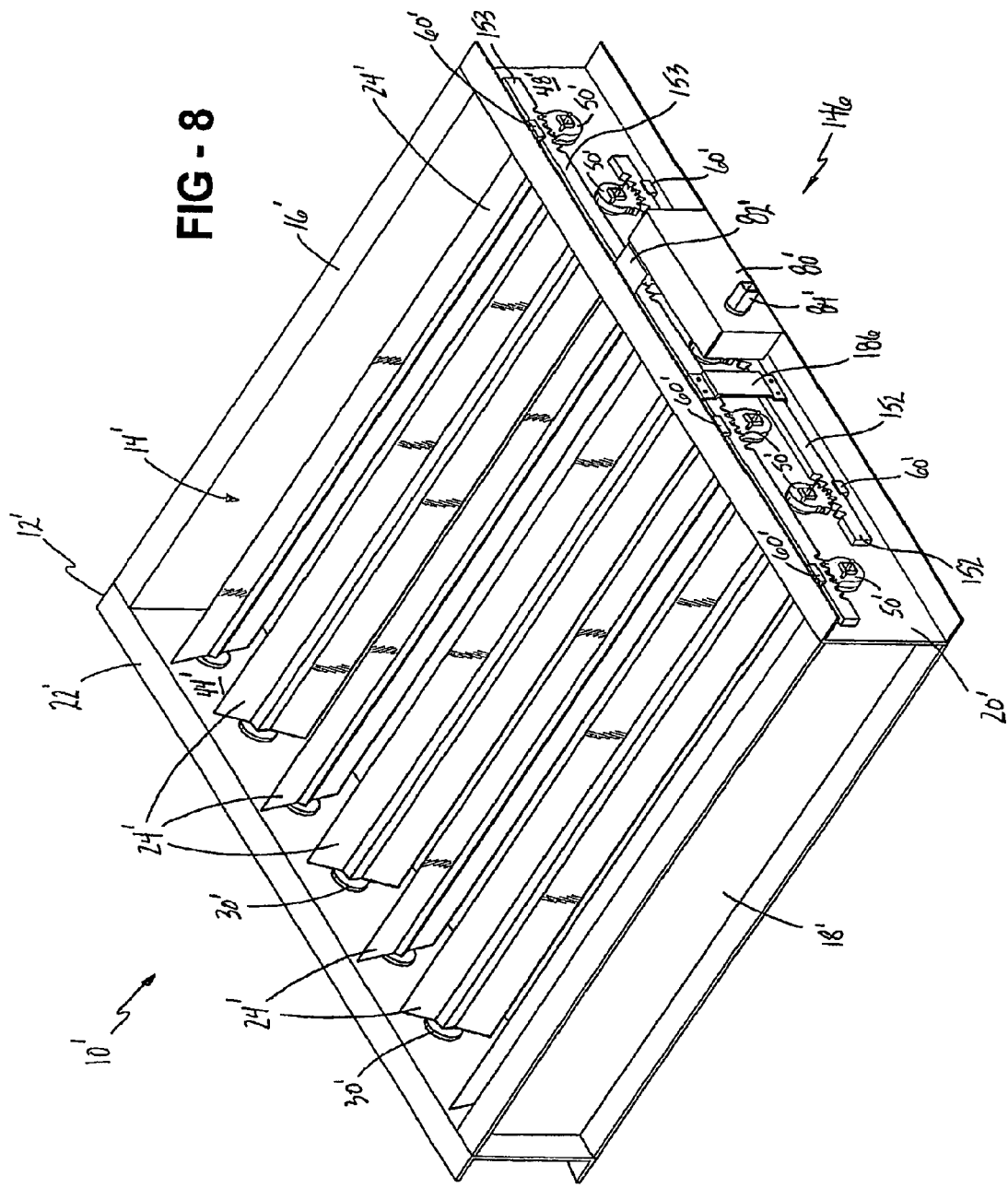
FIG. 8 is a perspective view of an air damper assembly including a drive mechanism according to a second embodiment of the invention.
Figure 9:
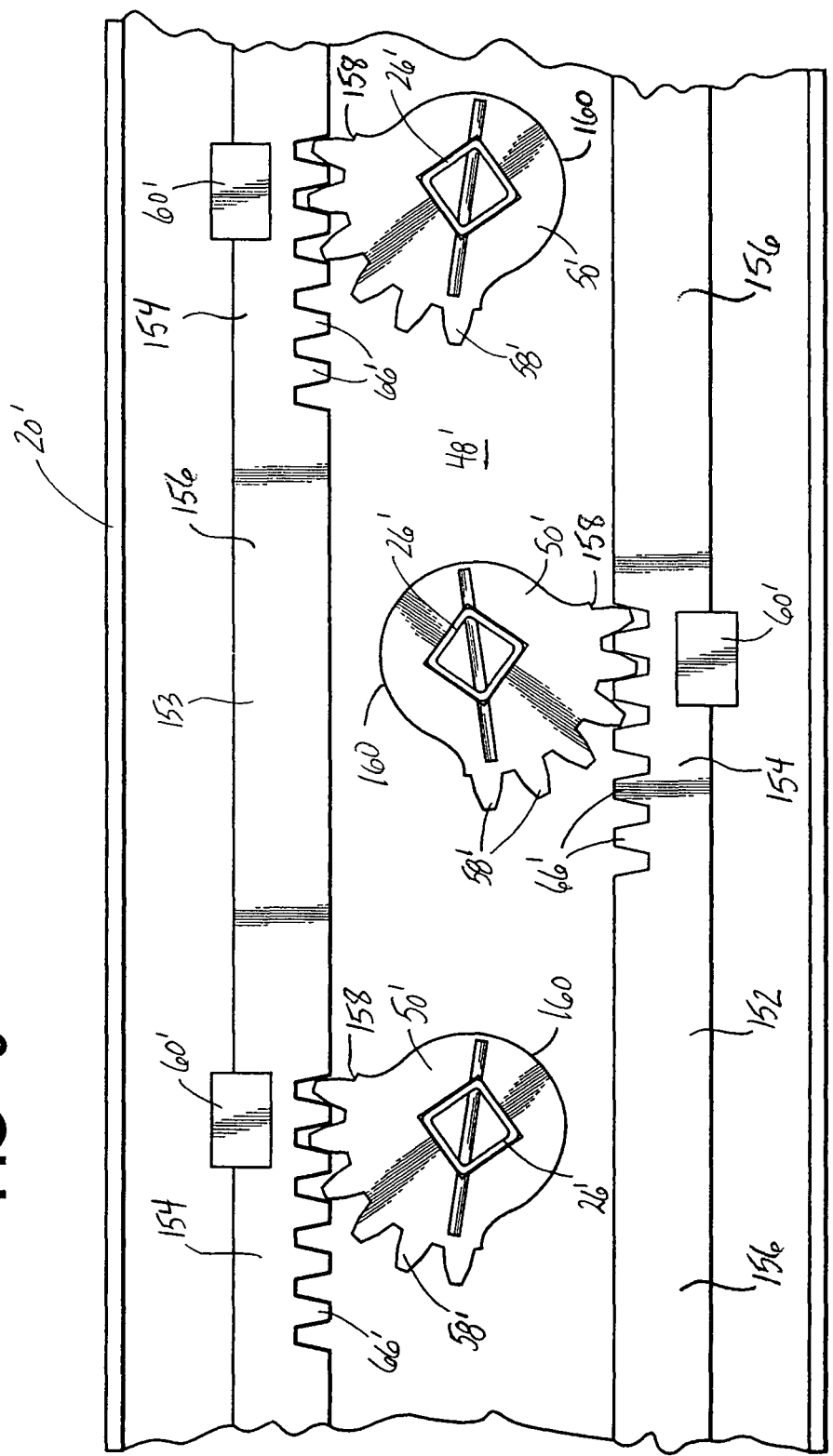
FIG. 9 is an enlarged, partially cut-away, side view of the air damper assembly of FIG. 8.

Referring to FIGS. 8 and 9, wherein like primed reference numerals represent similar elements as those described above, in a second embodiment of the invention the air damper assembly 10' includes a plurality of opposed damper blades 24'. More specifically, damper blades 24' on adjacent shafts 26' are oriented such that adjacent damper blades 24' rotate in opposite directions between the open and closed positions.

As described above, the flow area of the air inlet opening 14' is maximized when the damper blades 24' are rotated to the open position, whereat the damper blades 24' are substantially coplanar with the air flow. Contrarily, the flow area of the air inlet opening 14' is minimized, or even sealed tight, when the damper blades 24' are rotated to the closed position, whereat the damper blades 24' are transverse to the air flow.

The damper blades 24' are operatively coupled together and are rotated simultaneously between the open and closed positions by a drive mechanism, generally shown at 146. The drive mechanism 146 is located along an exterior surface 48' of the side member 20' of the frame 12'. The drive mechanism 146 includes a plurality of gears 50' supported by the shafts 26', a first elongated rack 152 extending along one side of the gears 50', and a second elongated rack 153 extending along an opposite side of the gears 50'. The first 152 and second 153 racks are connected by a plurality of brackets 186 (one shown) such that the first 152 and second 153 racks move together in the same direction. It is appreciated that the number of brackets 186 will depend on the length of the first 152 and second 153 brackets.

As described above with respect to the first embodiment, the first 152 and second 153 racks are slidably supported by a plurality of rack supports 60' fixedly secured to the side member 20' of the frame 12'. In the embodiment shown, the number of rack supports 60' for the first rack 152 corresponds to the number of gears 50' that meshingly engage the first rack 152 such that there is one rack support 60' located directly below each one of the gears 50'. It is appreciated, however, that more or less rack supports 60' can be used for supporting the first rack 152 without varying from the scope of the invention. Similarly, the number of rack supports 60' for the second rack 153 corresponds to the number of gears 50' that meshingly engage the second rack 153 such that there is one rack support 60' located directly above each one of the gears 50'. It is appreciated, however, that more or less rack supports 60' can be used for supporting the second rack 153 without varying from the scope of the invention.

The rack teeth 66' of the first 152 and second 153 racks are located along a plurality of toothed sections 154. Each toothed section 154 is spaced apart by an un-toothed section 156, the purpose of which will be apparent below.

Each gear 50' includes a peripheral portion 158 on which the gear teeth 58' are located and a peripheral portion 160 without any gear teeth. The gears 50' are oriented such that the gear teeth 58' meshingly engage the rack teeth 66' on the plurality of toothed sections 154 of the respective first 152 and second 153 racks. As such, the peripheral portion 160 of the gears 50' without any gear teeth corresponds to one of the un-toothed sections 156 of the respective first 152 and second 153 racks to prevent interference between the gears 50' and both of the first 152 and second 153 racks. More specifically, because both the first 152 and second 153 racks extend the length of the frame 12', generally between the top 16' and bottom 18' members, both the first 152 and second 153 racks are disposed adjacent to each of the gears 50'. Thus, if the gear teeth 58' surrounded the entire periphery of each gear 50', each gear 50' would interfere with both the first 152 and second 153 tracks, thereby rendering the air damper assembly 10' inoperable.

The gears 50' on adjacent shafts 26' are oriented such that the gear teeth 58' of adjacent gears 50' meshingly engage the rack teeth 66' of different racks and therefore rotate in opposite directions. For example, in the embodiment shown, the gear 50' nearest the top member 16' of the frame 12' meshingly engages the second rack 153 while the next gear 50' adjacent thereto meshingly engages the first rack 152, and so forth. Since the first 152 and second 153 racks are connected by the brackets 186 it is therefore appreciated that linear movement of the first 152 and second 153 racks toward the top member 16' of the frame 12' will result in the gears 50' that are engaging the first rack 152 rotating in a counterclockwise direction and the gears 50' that are engaging the second rack 153 rotating in a clockwise direction. Similarly, linear movement of the first 152 and second 153 racks toward the bottom member 18' of the frame 12' will result in the gears 50' that are engaging the first rack 152 rotating in the clockwise direction and the gears 50' that are engaging the second rack 153 rotating in the counterclockwise direction.

As described above with respect to the first embodiment, the fit of the first 152 and second 153 racks and the respective gears 50' is designed to eliminate almost all of the backlash. Any remaining backlash between the first 152 and second 153 racks and the respective gears 50' is eliminated by holding tight tolerances on the machining of the gears 50', the first 152 and second 153 racks, and the rack supports 60'. Finally, the spacing that is held between a rack support slot 79' and a centerline CL' of the bores 28' establishes an interference fit between the first 152 and second 153 racks and the respective gears 50'. Similarly, the flexibility of the rack supports 60' will absorb any deflection caused by the interference fit.

In operation, the electric drive 80' is actuated to rotate the damper blades 24' between the open and closed positions. Beginning with the damper blades 24' in the closed position, the electric drive 80' is actuated in a first direction such that the shaft 26' with the extended portion 84' rotates in the counterclockwise direction. Counterclockwise rotation of the shaft 26' with the extended portion 84' causes the gear 50' mounted thereon to also rotate in the counterclockwise direction. Meshing engagement between the gear teeth 58' of the gear 50' mounted on the shaft 26' with the extended portion 84' and the rack teeth 66' of the first rack 152 forces the first 152 and second 153 racks to move linearly toward the top member 16' of the frame 12' because the first 152 and second 153 racks are connected. This linear movement of the first rack 152 and meshing engagement between the rack teeth 66' of the first rack 152 and the gear teeth 58' of each gear 50' that is engaging the first rack 152 then causes such plurality of gears 50' to rotate in the counterclockwise direction and such damper blades 24' to also rotate in the counterclockwise direction to the open position. At the same time, this linear movement of the second rack 153 and meshing engagement between the rack teeth 66' of the second rack 153 and the gear teeth 58' of each gear 50' that is engaging the second rack 153 then causes such plurality of gears 50' to rotate in the clockwise direction and such damper blades 24' to also rotate in the clockwise direction to the open position.

To return the damper blades 24' to the closed position, the electric drive 80' is actuated in a second direction such that the shaft 26' with the extended portion 84' rotates in the clockwise direction. Clockwise rotation of the shaft 26' with the extended portion 84' causes the gear 50' mounted thereon to also rotate in the clockwise direction. Meshing engagement between the gear teeth 58' of the gear 50' mounted on the shaft 26' with the extended portion 84' and the rack teeth 66' of the first rack 152 forces the first 152 and second 153 racks to move linearly toward the bottom member 18' of the frame 12' because the first 152 and second 153 racks are connected. This linear movement of the first rack 152 and meshing engagement between the rack teeth 66' of the first rack 152 and the gear teeth 58' of each gear 50' that is engaging the first rack 152 then causes such plurality of gears 50' to rotate in the clockwise direction and such damper blades 24' to also rotate in the clockwise direction to the closed position. At the same time, this linear movement of the second rack 153 and meshing engagement between the rack teeth 66' of the second rack 153 and the gear teeth 58' of each gear 50' that is engaging the second rack 153 then causes such plurality of gears 50' to rotate in the counterclockwise direction and such damper blades 24' to also rotate in the counterclockwise direction to the closed position.

The invention has been described in an illustrative manner, and it is to be understood that the terminology, which has been used, is intended to be in the nature of words of description rather than of limitation. Many modifications and variations of the present invention are possible in light of the above teachings. It is, therefore, to be understood that within the scope of the appended claims, the invention may be practiced other than as specifically described.

What is claimed:

1. An air damper assembly for regulating an air flow, comprising:
   a frame adapted to be mounted in relationship to the air flow;
   a plurality of elongated damper blades rotatably mounted to said frame for rotational movement between an open position and a closed position;
   a gear fixedly secured to a distal end of each one of said plurality of damper blades, each said gear having a plurality of teeth;
   an elongated rack slidably coupled to said frame, said rack having a plurality of teeth;
   a plurality of flexible rack supports fixedly secured to said frame at predetermined positions, each rack support consisting of a single flexible member defining a channel that slidably supports the rack and a clip that secures the rack support to the frame, wherein the position of said rack supports establishes a vertical spacing between said rack and a centerline of said gears, said position of the rack supports and the spacing defining an interference fit between said teeth of said rack and said teeth of said gears;
   a drive mechanism for effecting movement of said plurality of damper blades between said open and closed positions;
   wherein the interference fit substantially eliminates backlash among said rack and gears; and
   wherein linear movement of said rack in a first linear direction results in rotational movement of said plurality of damper blades in a first rotational direction and linear movement of said rack in a second linear direction opposite said first linear direction results in rotational movement of said plurality of damper blades in a second rotational direction opposite said first rotational direction.

2. An air damper assembly as set forth in claim 1 wherein each of said plurality of damper blades includes a shaft extending longitudinally therethrough into said frame so that said plurality of damper blades is rotatably mounted to said frame and said gears are fixedly secured to a distal end of each of said shafts.

3. An air damper assembly as set forth in claim 2 wherein said shafts extend through bushings disposed in bores through said frame, said bushings machined from ultra high molecular weight polyethylene.

4. An air damper assembly as set forth in claim 3 wherein said rack support slots and said bores in said frame establish said vertical spacing between said rack and said centerline of said gears.

5. An air damper assembly as set forth in claim 4 including an actuator operatively coupled to one of said shafts to rotate said shaft in either said first or second rotational direction thereby actuating said plurality of damper blades between said open and closed positions.

6. An air damper assembly as set forth in claim 3 wherein each of said bushings includes an aperture for receiving said shaft therethrough and first and second portions defining a shoulder therebetween, said first portion rotatably disposed in said bore and spacing said gear from an exterior surface of said frame, said shoulder abutting an interior surface of said frame, and said second portion spacing said damper blade from said interior surface of said frame.

7. An air damper assembly as set forth in claim 2 wherein said shafts extend through bushings disposed in bores through said frame, said bushings machined from ultra high molecular weight polyethylene.

8. An air damper assembly as set forth in claim 1 wherein each of said plurality of rack supports is clipped into a rack support slot in said frame.

9. An air damper assembly as set forth in claim 8 wherein said plurality of rack supports is machined from ultra high molecular weight polyethylene.

10. An air damper assembly as set forth in claim 1, further including a second elongated rack slidably coupled to said frame and fixedly secured to said first rack, said second rack including a plurality of teeth.

11. An air damper assembly as set forth in claim 10 wherein vertical spacing between said second rack and said centerline of said gears defines an interference fit between said teeth of said second rack and said teeth of said gears.

12. An air damper assembly as set forth in claim 10 wherein said second rack includes a plurality of toothed sections and un-toothed sections, said plurality of teeth of said second rack being defined by said toothed sections of said second rack.

13. An air damper assembly as set forth in claim 1 wherein said plurality of rack supports is machined from ultra high molecular weight polyethylene.

14. An air damper assembly as set forth in claim 1 including an actuator operatively coupled to said drive mechanism for actuating said plurality of damper blades between said open and closed positions.

15. An air damper assembly as set forth in claim 1 wherein each said gear has a circumference and said plurality of teeth are provided only along part of said circumference, such that each said gear includes a peripheral portion with a plurality of teeth and a peripheral portion without teeth.

16. An air damper assembly as set forth in claim 1 wherein each said rack includes a plurality of toothed sections and un-toothed sections, said plurality of teeth of said rack being defined by said toothed sections.

* * * * *